United States Patent [19]

Rainin

[11] 4,338,687
[45] Jul. 13, 1982

[54] INTRAOCULAR LENS WITH SPRING MECHANISM

[76] Inventor: Edgar A. Rainin, 20 Shawn Ct., Danville, Calif. 94526

[21] Appl. No.: 196,281

[22] Filed: Oct. 14, 1980

[51] Int. Cl.³ ............................ A61F 1/16; A61F 1/22
[52] U.S. Cl. .......................................................... 3/13
[58] Field of Search .......................................... 3/13, 1

[56] References Cited

U.S. PATENT DOCUMENTS

| | | | |
|---|---|---|---|
| 4,134,161 | 1/1979 | Bayers | 3/13 |
| 4,159,546 | 7/1979 | Shearing | 3/13 |
| 4,254,509 | 3/1981 | Tennant | 3/13 |
| 4,254,510 | 3/1981 | Tennant | 3/13 |

*Primary Examiner*—Ronald L. Frinks
*Attorney, Agent, or Firm*—Bielen & Peterson

[57] ABSTRACT

An intraocular lens utilizing a lens portion or optical zone. An appendage is coupled to the lens portion and extends away from the same to the periphery of the eye. A spring mechanism used in conjunction with the lens portion permits resilient movement of the appendage in relation to the lens portion when forces are exerted on the appendage.

9 Claims, 5 Drawing Figures

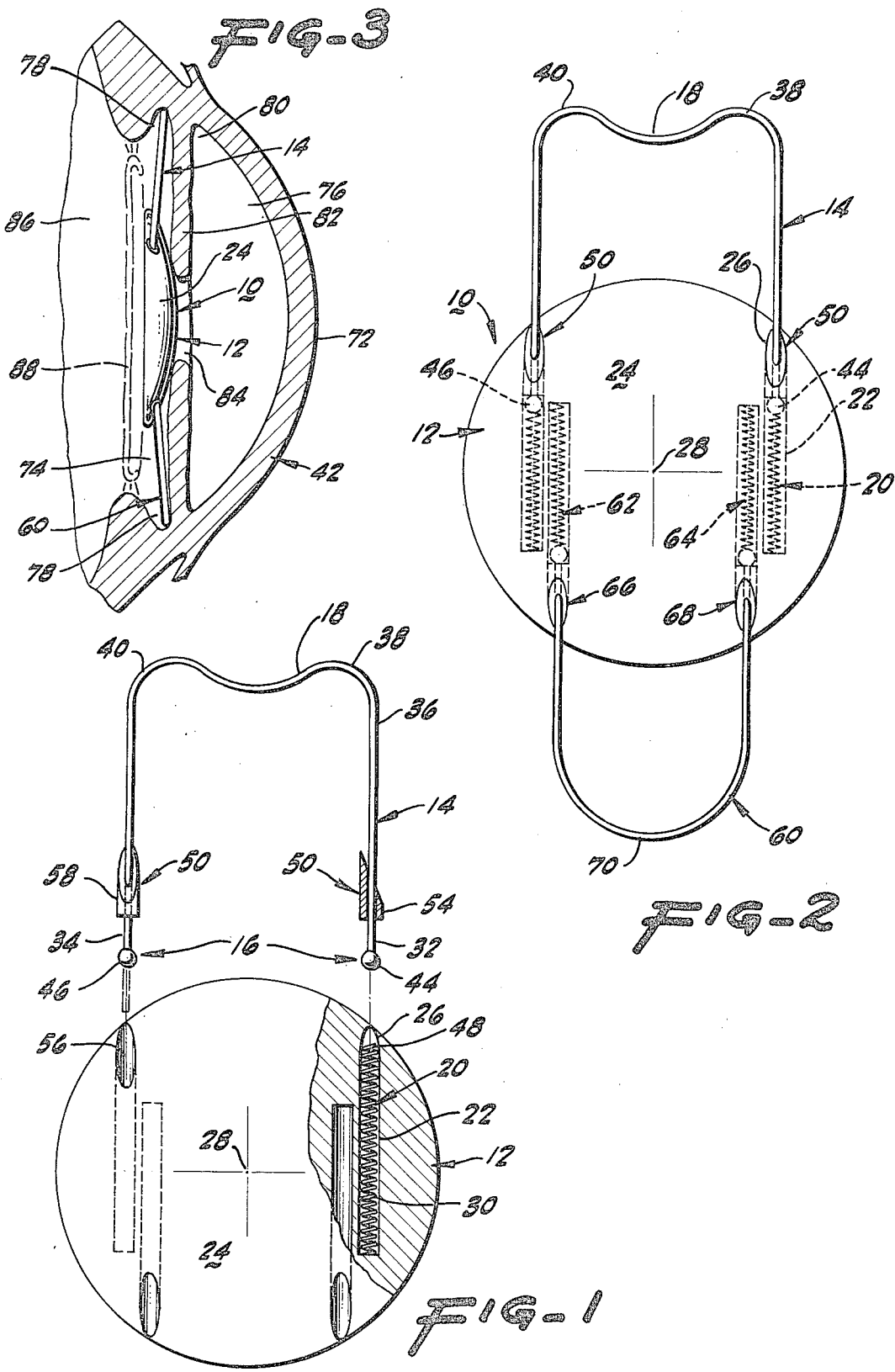

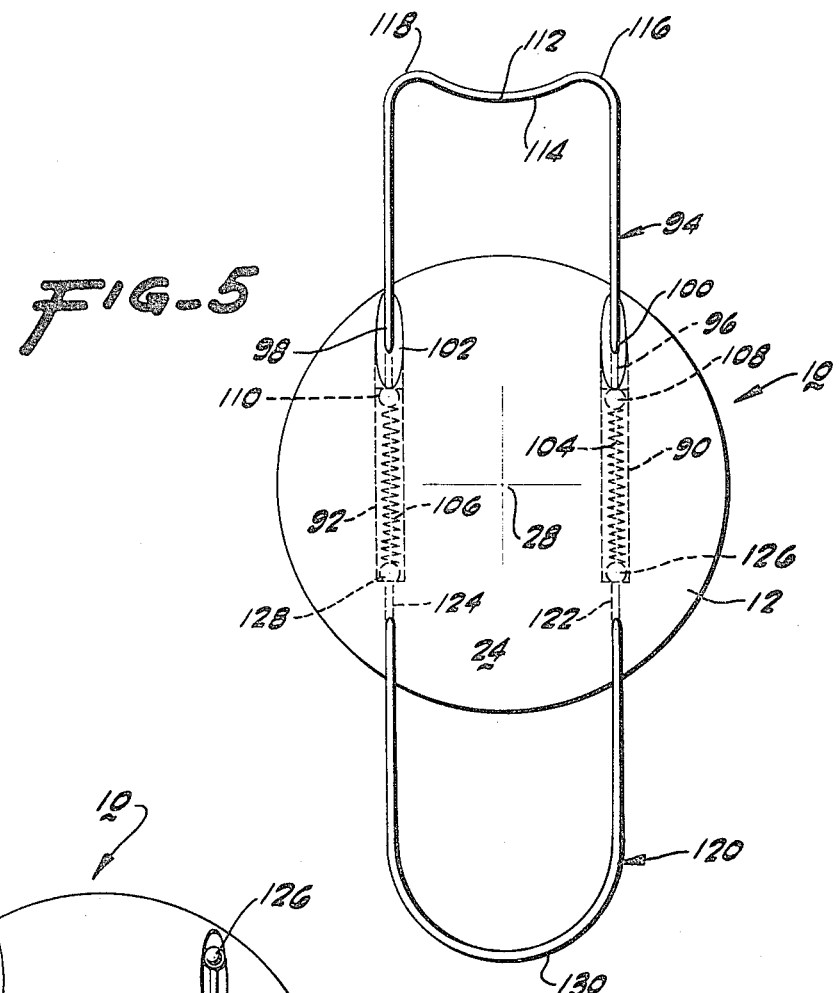
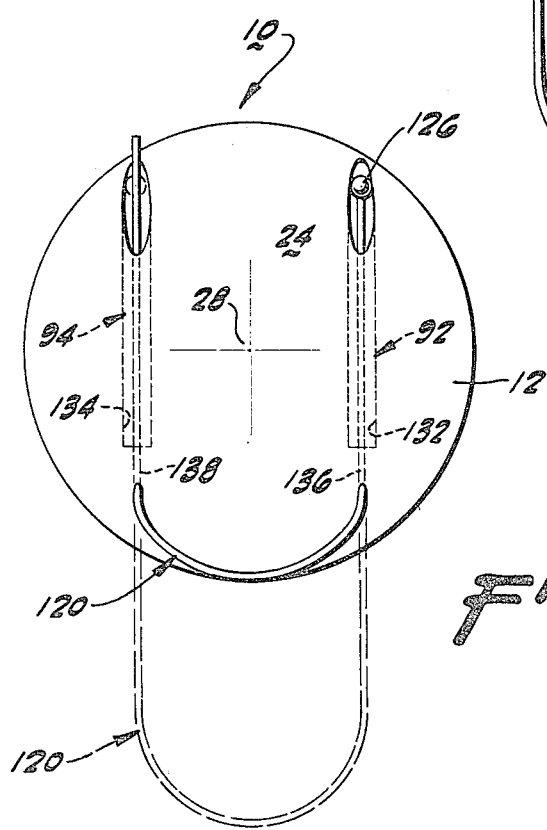

INTRAOCULAR LENS WITH SPRING MECHANISM

BACKGROUND OF THE INVENTION

The present invention relates to a novel intraouclar lens having a resiliently movable appendage.

Intraocular lenses have proved to be a superior method of correction of vision after a cataract operation. Although many intraocular lenses have been proposed and developed with a good degree of success, a problem of adjustability remains with intraocular lenses placed in the eye in either the anterior or posterior chamber thereof. This problem is especially acute with fixation of the intraocular lens at the peripheral portion of the eye, namely the angle of the anterior chamber or the ciliary sulcus of the posterior chamber. Reference is made to U.S. Pat. No. 4,159,546 issued to Shearing which discribes an intraocular lens having a pair of springy legs. The Shearing lens is restricted to use after extra capsular cataract surgery and is normally placed in the posterior chamber. The Shearing lens is quite difficult to insert directly into the ciliary sulcus since the surgeon performing the operation is not able to see the springy arms during insertion of the lens.

Each intraocular lens implanted must be properly sized for insertion, which has proved to be a difficult task. Firstly, measurement of the anterior chamber dimensions cannot be accurately determined without surgically entering the eye. Also, the eye changes shape depending on the amount of aqueous humor present therein. Reference is made to U.S. Pat. No. 4,134,161 which proposes a solution to adjusting of the size of an intraocular lens. Also, U.S. patent application Ser. No. 054,953 filed July 5, 1979 represents a step in the evolution of adjustable appendages for intraocular lenses. However, the lens described in the above reference requires a resilient appendage for its workability.

A lens which has adjustable appendages and is capable of using rigid loop material and possesses the ability to provide three point fixation would be highly desirable in the medical field.

SUMMARY OF THE INVENTION

In accordance with the present invention a novel and useful intraocular lens for implantation in the eye having adjustable appendages is provided.

The lens of the present invention utilizes a lens portion or optical zone which may be constructed of any optical material which is non-reactive to biological tissue. An appendage is associated with the lens and extends away from the same to the periphery or peripheral portions of the eye such as the angle of the anterior chamber or the ciliary sulcus of the posterior chamber. The appendage is coupled to the lens portion and may be formed of an elongated member having a proximal and distal end portion.

The lens of the present invention also embraces spring means associated with the lens portion which permits resilient movement of the appendage in relation to the lens portion. The appendage may be formed into a closed or open loop configuration.

The spring means may take the form of first providing a cavity defining an opening in the lens portion. The opening has at least a portion thereof providing a continuous peripheral wall area extending along the length of the cavity. The appendage may be deemed to include a proximal and distal end portion in relation to the lens portion. A spring may be partially housed in the lens portion opening and extend along the continuous peripheral wall area and be adapted for receiving force exerted on the appendage and transmitted by the proximal end portion of the appendage. Likewise, the appendage may be formed into a closed loop such that the proximal end portion of the appendage includes a first and second end and the distal end portion of the appendage includes a continuous member between the first and second end. In such a case, the lens portion would include a first and second opening and a first and second spring housed therein, respectively. Each of the ends of the appendage would be capable of exerting force on the first and second springs resulting in resilient movement of the appendage in relation to the lens portion. Further, a pair of appendages may be provided operating in the same manner as the appendage hereinabove described.

The means for coupling the appendage with the lens may include providing the first end of the appendage with an enlargement which would be placed within the first opening in the lens portion. Moreover the first opening may be provided with restriction means for preventing the passage of the end enlargement from the first opening. Such a restriction may take the form a bushing which is threaded over the appendage and later fixed to the walls of the first opening in the lens portion.

The invention of the present application may also be deemed to include a method of producing an intraocular lens which includes the steps of forming an opening in the lens portion and inserting the first end portion of the elongated member into a bushing. The bushing would permit the elongated member to move within the same. The first end of the elongated member would be enlarged to prevent removal of the bushing from the appendage. A spring would be inserted within the opening formed in the lens portion. Such a spring would be capable of acting resiliently in response to any force exerted by the first end of the appendage. The first end portion of the elongated member is inserted into the first opening adjacent the spring and the bushing is then fastened to the lens portion thus trapping the enlarged end of the appendage within the first opening in the lens portion. Again, the other end of the appendage may be resiliently attached to the lens portion in the same manner as hereinabove described in relation to the first end of the appendage.

It may be apparent that a novel and useful intraocular lens structure having at least one resilient appendage has been described.

It is therefore an object of the present invention to provide an intraocular lens which includes at least one appendage which will absorb any force exerted on the appendage and change the overall dimension of the intraocular lens in relation to such force.

It is another object of the present invention to provide an intraocular lens which does not require the use of a flexible loop material to form any appendages or legs extending from the lens portion of the intraocular lens.

It is another object of the present invention to provide and intraocular lens which is centered easily within the eye and may provide three point fixation in combination with at least one resilient appendage.

It is still another object of the present invention to provide an intraocular lens which is capable of having a substantial range of flexing while remaining centered along the optical axis of the eye.

A further object of the present invention is to provide an intraocular lens which may be simply and economically manufactured and reduce the inventory of different sized lenses necessary for proper performance of intraocular lens implantation operations by a physician.

The invention possesses other objects and advantages especially as concerns particular charateristics and features thereof, which will become apparent as the specification continues.

BRIEF DESCRIPTION OF THE DRAWINGS

FIG. 1 is a top plan view with a broken away portion revealing an opening in the lens portion of the intraocular lens of the present invention.

FIG. 2 is a top plan view of an intraocular lens having a pair of resiliently mounted appendages.

FIG. 3 is a sectional view of an eye showing the lens of the present invention placed within the posterior chamber of the eye.

FIG. 4 is a top plan view of a second embodiment showing the assembly of one appendage to the lens portion.

FIG. 5 is a top plan view of the second embodiment showing a completed intraocular lens with a pair of resiliently mounted appendages.

Various aspects of the present invention will evolve from the following detailed description of the preferred embodiments thereof, which should be taken into conjunction with the hereinabove described drawings.

DESCRIPTION OF THE PREFERRED EMBODIMENTS

For a better understanding of the invention reference is made to the following detailed description which should be referenced to the hereinabove described drawings.

The invention as a whole is represented in the drawings by reference character 10 and includes as one of its elements a lens portion or optical zone 12. Lens portion 12 may be constructed of any biologically inert, transparent material such as methylmethacrylate, quartz, ophthalmic glass, and other materials known in the optical art. Lens portion 12 may include an appendage 14, FIG. 1, which is associated with lens portion 12 and extends therefrom. Appendage 14 may include a proximal end portion 16 and a distal end portion 18 in relation to lens portion 12. Appendage 14 may be formed of biologically inert and non-absorptive material in relation to living tissue. Again, appendage 14 may be formed of methylmethacrylate, platinum, and other materials known in the art of intraocular lens manufacture.

The intraocular lens 10 also has as one of its elements spring means 20 for permitting the resilient movement of appendage 14 in relation to lens portion 12. Spring means 20 is associated with lens portion 12 in that spring means 20 may take the form of providing an opening 22 in lens portion 12. As the surface 24 of lens portion 12 is curved, FIG. 3, opening 22 appears to have an oval entrance 26 when viewed from directly above the same. Opening 22 may extend a predetermined distance into lens portion 12 preferably away from optical axis 28, FIG. 1. In this manner, spring means 20 will not interfere with the optical rectification afforded by lens portion 12. A first spring 30 which may take any form of a member which exerts a resilient force, is at least partially housed within opening 22. As shown in the preferred embodiments, FIGS. 1–3, first spring 30 takes the form of a coiled body which may constructed of a springy, non-reactive material such as plastic, metal, and like. Spring 30 is adapted for receiving any force exerted by proximal end 16 of appendage 14, the details of which will be explained hereinafter.

Appendage 14 may take the form of an open or closed loop, but is shown in the preferred embodiment as a closed looped member to obviate the disadvantages of a bitter end, namely, destruction of tissue, hooking onto intraocular structures before fixation, and the like. Proximal end portion 16 may include a first end 32 and a second end 34. Intermediate portion 36 spans ends 32 and 34. Pair of of protuberences 38 and 40 may be formed in intermediate portion 36 to provide two points of the fixation of lens 10 within eye 42, which will be explained in further detail as the specification continues. First end 32 of proximal end portion 16 may be formed with end enlargement 44. Likewise, end 34 of proximal end portion 16 may be informed with a similar enlargement 46. Enlargements 44 and 46 may take the form a sphere which is fixed to end portions 32 and 34 or created in situ by heating ends 32 and 34 with a heat source such as a laser, ultrasonic welding device, and the like. Enlargement 44 is sized to fit within opening 22 and to bear on the end 48 of first spring 30. Thus, any forces acting on distal end portion 18 of appendage 14 and transmitted to proximal end portion 16 would be transferred to spring 30.

The lens of the present application also includes means for coupling appendage 14 to lens portion 12. Such coupling means may take the form of placement of enlargement 44 within opening 22 and employing restriction means for preventing the passage of enlargement 44 from the same. Such restriction means may include a bushing 54 which fits over end 32 of proximal end portion 16, before the formation of enlargement 44, and which permits free relative movement between appendage 14 and bushing 54. Bushing 54 would be sized to fit snugly within opening 22 and be fixed to the walls of opening 22 by any suitable fastening means.

By the same analogy, end 34 of proximal end portion 16 may be coupled to lens portion 12 via opening 56 and bushing 58. Since the structure of spring means 20, and coupling means 50, with reference to first end 32 of proximal end portion 16, are identical to the spring and coupling means associated with second end 34 of proximal end portion 16, no further details will be provided hereinafter.

Turning to FIG. 2, it may be seen that a second appendage 60 utilizing spring means 62 and 64 and coupling means 66 and 68, extends from lens portion 12 in a direction different from appendage 14. Again, the fixation of appendage 60 would be similar to the fixation of appendage 14 in relation to lens portion 12. Appendages 14 and 60 need not br resilient and could be formed of rigid material. Moreover, resilient material may be used also to form these appendages if so desired. Appendage 60 includes a bowed portion 70, combined with protuberances 38 and 40 would create a three point fixation within the eye after implantation of lens 10.

FIGS. 4 and 5 depict another embodiment of intraocular lens 10 which includes lens portion 12 having openings 90 and 92 therethrough. First appendage 94 has ends 96 and 98 within bushings 100 and 102. Springs 104 and 106, FIG. 5, lie within openings 90 and 92, respectively, to exert a spring force against enlargements 108 and 110 found on the termini of ends 96 and 98. Intermediate portion 112 of appendage 94 includes a bowed portion 114 between two promontories 116 and 118. A second appendage 120 includes ends 122 and 124 possessing enlargements 126 and 128. Intermediate portion 130 is shown as curved but could take the voluted shape of first appendage 94 if desired. Second appendage bears on springs 104 and 106, also.

The lens 10 of the present invention, as shown in FIGS. 1–3, may be formed from a lens portion 12 and elongated member such as appendage 14, having ends 32 and 34. Such a method may proceed by forming an opening 22 in lens portion 12. End 32 would be inserted into bushing 54 such that appendage 14 is freely movable within the bushing 54. End 32 would then be provided with an enlargement 44 which would prevent the removal of bushing from appendage 14. Spring 30 is then inserted within opening 22 and end 32 is placed adjacent spring 30 within opening 22. Preferably, spring 30 would be slightly compressed at this point. Bushing 54 would then be fastened to lens portion 12 at the periphery of opening 22. It may be apparent that the same method would apply for the resilient fixation of end 34 of appendage 14 as well as both ends of appendage 60.

Turning to FIG. 3, it may be seen in operation, the surgeon would select an intraocular lens having the proper optical characteristics beneath cornea 72 in the posterior chamber 74 or anterior 76 of eye 42. Appendages 14 and 60 wedge into the ciliary sulcus 78 or at the angle 80 as desired. Thus, lens portion 12 would lay adjacent iris 82 and cover the pupil 84. Lens 10 possesses the adjustability as to its overall size which would accomodate any changes in the size of eye 42. More pressure is exerted by the vitreous humor 86 behind the natural lens remnant 88 of an extra capsular surgical procedure.

The embodiment illustrated in FIGS. 4 and 5 may be formed by drilling openings 92 and 94 such that openings 92 and 94 include a large chamber 132 and 134, a small chamber 136 and 138, respectively. Such a configuration for openings 92 and 94 may be easily accomplished by countersinking a drill from the top of the lens 10 of FIG. 4. Second appendage 120 is inserted through small chambers 136 and 138, large chambers 132 and 134, to the exterior of openings 92 and 94. Enlargements 126 and 128 are formed (only enlargement 126 shown in FIG. 4), by any method as described heretofore in relation to enlargements 44 and 46. Appendage 120 and enlargements 126 and 128 are then forced back into openings 92 and 94 and are held within large chambers 132 and 134 by the tapering structure interfacing with small chambers 136 and 138; the position of appendage 120 being depicted in phantom at this position. Springs 104 and 106 are inserted into openings 92 and 94 and first appendage is coupled to lens portion 12 as described hereinbefore relative to appendage 14. The embodiment of FIGS. 4 and 5 embraces the coupling and spring means described in relation to the embodiment of FIGS. 1, 2, and 3.

While in the foregoing embodiments of the invention have been set forth in considerable detail for the purposes of making a complete disclosure of the invention, it will be apparent to those of ordinary skill in the art that numerous changes may be made in such details without departing from the spirit and principles of the invention.

What is claimed is:

1. An intraocular lens comprising:
   a. a lens portion;
   b. an appendage associated with said lens portion and extending away from said lens portion, said appendage including a proximal and a distal end portion;
   c. means for coupling said proximal end portion of said appendage with said lens portion with said distal end portion of said appendage extending away from said lens portion;
   d. spring means associated with said lens portion for permitting resilient movement of said appendage in relation to said lens portion, said spring means including a cavity within said lens portion, at least a portion of said cavity including a continuous peripheral wall area extending along the length of said cavity, and a spring being at least partially housed within said lens portion cavity and extending along said continuous peripheral wall area, said spring being adapted for receiving force exerted by said proximal end portion of said appendage.

2. The intraocular lens of claim 1 in which said appendage includes a looped member formed by said proximal end portion of said appendage including a first and a second end, and said distal end portion of said appendage includes a portion intermediate said first and second ends and said spring means includes said spring being a first spring and said cavity being a first cavity and additionally includes second cavity and a second spring housed therein, each of said ends of said appendage being capable of exerting force on said first and second springs housed in said first and second cavities in said lens portion, respectively.

3. The intraocular lens of claim 2 in which said means for coupling said appendage with said lens portion comprises providing at least said first end of said appendage with an enlargement for placement within said first cavity and further providing said first cavity with restriction means for preventing the passage of said end enlargement from said first cavity.

4. The intraocular lens of claim 1 in which said appendage is a first appendage and which additionally comprises a second appendage associated with said lens portion and extending therefrom.

5. The intraocular lens of claim 4 in which said spring means comprises spring means for permitting resilient movement of said first and second appendages in relation to said lens portion.

6. The intraocular lens of claim 5 in which said first and second appendages each include a proximal and a distal end portion and said spring means includes at least one cavity in said lens portion and at least one spring being at least partially housed therein; said at least one spring being adapted for receiving force exerted by said proximal end portions of said first and second appendages.

7. The intraocular lens of claim 6 in which said first and second appendages each includes a looped member formed by said proximal end portion of said each appendage including a first and a second end, and said distal end portion of said each appendage including a portion intermediate said first and second ends and said spring means including said lens portion including a first and second cavity having a first and second spring housed therein, respectively, said first and second ends of said each appendage being capable of exerting force on said first and second springs housed in said first and second cavities in said lens portion, respectively.

8. The intraocular lens of claim 7 in which said spring means further includes a third and fourth spring at least partially housed in a third and fourth cavity in said lens portion, said first and second ends of said first appendage being capable of exerting force on said first and second springs, respectively, and said first and second ends of said second appendage being capable of exerting force on said third and fourth springs, respectively.

9. The intraocular lens of claim 7 which additionally comprises means for coupling said second appendage with said lens portion and includes providing at least said first end of said second appendage with an enlargement for placement within at least said first cavity and further providing at least said first cavity with restriction means for preventing the passage of said end enlargement from said first cavity.

* * * * *